United States Patent
Black et al.

(10) Patent No.: US 10,018,748 B2
(45) Date of Patent: Jul. 10, 2018

(54) INLINE DENSITY AND FLUORESCENCE SPECTROMETRY METER

(71) Applicant: Saudi Arabian Oil Company, Dhahran (SA)

(72) Inventors: Michael John Black, Dhahran (SA); Talha Jamal Ahmad, Dhahran (SA); Mohamed Nabil Noui-Mehidi, Dhahran (SA)

(73) Assignee: Saudi Arabian Oil Company, Dhahran (SA)

(*) Notice: Subject to any disclaimer, the term of this patent is extended or adjusted under 35 U.S.C. 154(b) by 176 days.

(21) Appl. No.: 14/993,322

(22) Filed: Jan. 12, 2016

(65) Prior Publication Data

US 2016/0209542 A1    Jul. 21, 2016

Related U.S. Application Data

(60) Provisional application No. 62/104,272, filed on Jan. 16, 2015.

(51) Int. Cl.
*G01N 23/083* (2018.01)
*G01V 5/12* (2006.01)
(Continued)

(52) U.S. Cl.
CPC .............. *G01V 5/125* (2013.01); *G01N 23/12* (2013.01); *G01N 23/223* (2013.01); *G01N 33/2823* (2013.01); *G01N 33/2847* (2013.01)

(58) Field of Classification Search
CPC ......... G01N 2223/076; G01N 33/2823; G01N 2223/637; G01N 33/487; G01N 21/85
(Continued)

(56) References Cited

U.S. PATENT DOCUMENTS

| 5,689,540 A | 11/1997 | Stephenson et al. |
| 7,507,952 B2 | 3/2009 | Groves et al. |

(Continued)

FOREIGN PATENT DOCUMENTS

| WO | 9317326 A1 | 9/1993 |
| WO | 2008032265 A1 | 3/2008 |

(Continued)

OTHER PUBLICATIONS

International Search Report and Written Opinion for related PCT application PCT/US2016/013591 dated Apr. 29, 2016.

*Primary Examiner* — Don Wong
(74) *Attorney, Agent, or Firm* — Bracewell LLP; Constance Gall Rhebergen; Linda L. Morgan

(57) ABSTRACT

Systems and methods for determining characteristics of a fluid in a subterranean well include providing a production pipe extending into the subterranean well to convey the fluids from within the subterranean well to an earth's surface. An x-ray source is located on a first side of the production pipe. An x-ray beam is directed into the production pipe, into the fluids, and out of an opposite side of the production pipe as a resulting beam, with the x-ray source. A level of attenuation of the resulting beam is detected with an attenuation detector located on an opposite side of the production pipe. A fluorescence spectra of the resulting beam is detected with a scattered fluorescence detector located on the opposite side of the production pipe. A fluorescence peak of the resulting beam is detected with a peak fluorescence detector located on the opposite side of the production pipe.

21 Claims, 2 Drawing Sheets

(51) Int. Cl.
  *G01N 23/12* (2018.01)
  *G01N 23/223* (2006.01)
  *G01N 33/28* (2006.01)

(58) Field of Classification Search
  USPC .......................... 378/6, 7, 53, 59, 44, 45, 48
  See application file for complete search history.

(56) References Cited

U.S. PATENT DOCUMENTS

| | | |
|---|---|---|
| 7,542,543 B2 | 6/2009 | Shampine et al. |
| 7,668,293 B2 | 2/2010 | Wraight et al. |
| 7,684,540 B2 | 3/2010 | Groves et al. |
| 7,903,782 B2 | 3/2011 | Groves et al. |
| 8,155,891 B2 | 4/2012 | Kong et al. |
| 8,300,769 B2 | 10/2012 | Kim et al. |
| 8,433,035 B2 | 4/2013 | Watanabe et al. |
| 8,582,717 B2 | 11/2013 | Ohzawa |
| 8,744,042 B2 * | 6/2014 | Ohzu .................. G01N 23/223 378/46 |
| 8,765,061 B2 | 7/2014 | Tunheim et al. |
| 2007/0189452 A1 | 8/2007 | Johnson et al. |
| 2012/0087467 A1 | 4/2012 | Tjugum |
| 2013/0112406 A1 | 5/2013 | Zuo et al. |
| 2014/0110105 A1 | 4/2014 | Jones et al. |
| 2015/0000902 A1 | 1/2015 | Pomerantz et al. |
| 2015/0040658 A1 | 2/2015 | Abyzov et al. |

FOREIGN PATENT DOCUMENTS

| | | |
|---|---|---|
| WO | 2012177472 A2 | 12/2012 |
| WO | 2014035287 A1 | 3/2014 |

\* cited by examiner

INLINE DENSITY AND FLUORESCENCE SPECTROMETRY METER

CROSS REFERENCE TO RELATED APPLICATIONS

This application claims priority to and the benefit of U.S. Provisional Application No. 62/104,272, titled "Inline Density And Fluorescence Spectrometry Meter," filed Jan. 16, 2015, the full disclosure of which is hereby incorporated by reference herein in its entirety.

BACKGROUND OF THE DISCLOSURE

1. Field of the Disclosure

The present disclosure relates generally to the measurement of fluids in a subterranean well, and more specifically to instrumentation and methods for real-time measurements of water cut and the composition of crude products and brine in hydrocarbon wells.

2. Description of the Related Art

Hydrocarbon reservoirs are typically considered to include reservoirs containing either oil, gas, or both as recoverable hydrocarbons. A water phase coexists with hydrocarbons in almost all hydrocarbon reservoirs. As producing time progresses the water production rate increases, compared to the simultaneously declining oil production rate. The relative water-oil production rates are monitored at individual producing wells and quantified through a parameter known in the petroleum industry as the water cut or water cut ratio. Tracking the water cut can be critical in the management of hydrocarbon reservoirs. Changes in the water cut can also be an indication of how the oil formation is swept by water injection. By tracking the water cut, decisions can be made to control rates from different perforation intervals within the producing wellbore for better management of sweep and recovery.

Salinity measurements and crude product characteristics of multiphase mixtures are highly demanded by daily operations for both reservoir management and production allocation in the oil and gas industry. Such information can be used, for example to find compositional gradients as well as to identify compartments and reservoir connectivity.

SUMMARY OF THE DISCLOSURE

Embodiments of the present disclosure provide methods and systems for simultaneously measuring the mean density of a multiphase fluid consisting of crude oil and brine, and at the same time performing chemical analysis on the crude product, such as an oil phase fraction, through chemometric x-ray fluorescence spectrometry. Additionally, embodiments of this disclosure can monitor brine ion composition through detection of specific x-ray fluorescence peaks. Methods and apparatuses described in this disclosure provide for measurement of water cut downhole without the need for radioactive sources, and will provide in-situ analysis of the chemical composition of produced crude as well as brine composition and hence an estimate of brine density. Embodiments of this disclosure can therefore determine characteristics of produced crude product, such as the relative density or the American Petroleum Institute gravity ("API") of the oil in the fluid, determine brine composition, and determine the density of the multiphase fluid, in a real time measurement.

In an embodiment of this disclosure, a method for determining characteristics of a fluid in a subterranean well includes providing a production pipe extending into the subterranean well to convey the fluids from within the subterranean well to an earth's surface. An x-ray source is located on a first side of the production pipe. An x-ray beam is directed into the production pipe and into the fluids, and out of an opposite side of the production pipe as a resulting beam, with the x-ray source. A level of attenuation of the resulting beam is detected with an attenuation detector located on an opposite side of the production pipe. A fluorescence spectra of the resulting beam is detected with a scattered fluorescence detector located on the opposite side of the production pipe. A fluorescence peak of the resulting beam is detected with a peak fluorescence detector located on the opposite side of the production pipe.

In alternate embodiments, the production pipe can have a source window through a sidewall on the first side of the production pipe and an outgoing window through the sidewall on the opposite side of the production pipe. The step of directing the x-ray beam into the production pipe can include passing the x-ray beam into the production pipe through the source window. The step of directing the x-ray beam out of an opposite side of the production pipe as a resulting beam can include passing the x-ray beam out of the production pipe through the outgoing window.

In other alternate embodiments, the step of directing the x-ray beam out of an opposite side of the production pipe as a resulting beam further includes directing an attenuation beam of the resulting beam through a detection window of the outgoing window, directing a scattered fluorescence of the resulting beam through a scattered fluorescence window of the outgoing window, and directing a specific fluorescence of the resulting beam through a specific fluorescence window of the outgoing window. The step of detecting the scattered fluorescence of the resulting beam can include detecting the scattered fluorescence having an energy of 18 to 23 keV. The step of detecting the fluorescence peak can include detecting the fluorescence peak with a wavelength of 1.191 nm.

In yet other alternate embodiments, a processor system can be in communication with the attenuation detector, the scattered fluorescence detector, and the peak fluorescence detector. A density of the fluid, a density of an oil of the fluid, and a concentration of an ion within a brine of the fluid can be determined with the processor system. A water cut value can be calculated with the density of the fluid, the density of the oil and the concentration of the ion with the processor system.

In an alternate embodiment of this disclosure, a method for determining characteristics of a fluid in a subterranean well includes locating an x-ray source on a first side of a production pipe. The production pipe extends into the subterranean well to convey the fluids from within the subterranean well to an earth's surface. An x-ray beam is directed with the x-ray source into the production pipe and into the fluids, and out of an opposite side of the production pipe as an attenuation beam, a scattered fluorescence, and a specific fluorescence. A level of attenuation of the attenuation beam can be detected with an attenuation detector and determining a density of the fluid from the level of attenuation. A fluorescence spectra of the scattered fluorescence can be detected with a scattered fluorescence detector and a density of an oil of the fluid can be determined with the fluorescence spectra. A fluorescence peak of the specific fluorescence can be detected with a peak fluorescence detector and a concentration of an ion within a brine of the fluid can be determined with the fluorescence peak.

In other embodiments, a water cut of the fluid can be determined using the level of attenuation, the fluorescence spectra and the fluorescence peak. A processor system can perform the steps of determining the density of the fluid, determining the density of the oil, and determining the concentration of the ion. The attenuation beam can be directed through a detection window of the production pipe. The scattered fluorescence can be directed through a scattered fluorescence window of the production pipe. The specific fluorescence can be directed through a specific fluorescence window of the production pipe.

In another alternate embodiment of the current application, a system for determining characteristics of a fluid in a subterranean well includes a production pipe extending into the subterranean well to convey the fluids from within the subterranean well to an earth's surface. An x-ray source is located on a first side of the production pipe directing an x-ray beam into the production pipe and into the fluids, and out of an opposite side of the production pipe as a resulting beam. An attenuation detector is located on an opposite side of the production pipe and is selectively detecting a level of attenuation of the resulting beam. A scattered fluorescence detector is located on the opposite side of the production pipe and is selectively detecting a fluorescence spectra of the resulting beam. A peak fluorescence detector is located on the opposite side of the production pipe and is selectively detecting a specific fluorescence of the resulting beam.

In alternate embodiments, the production pipe can have a source window through a sidewall on the first side of the production pipe and an outgoing window through the sidewall on the opposite side of the production pipe. The x-ray beam can pass into the production pipe through the source window and the resulting beam can pass out of the production pipe through the outgoing window. The outgoing window can have a detection window through which an attenuation beam of the resulting beam passes, a scattered fluorescence window through which the scattered fluorescence of the resulting beam passes, and a specific fluorescence window through which a fluorescence peak of the resulting beam passes. The scattered fluorescence window can be transparent to the scattered fluorescence having an energy of 18 to 23 keV. The specific fluorescence window can be transmissive to the wavelength of the specific fluorescence.

In other alternate embodiments, the specific fluorescence has a wavelength of 1.191 nm. The x-ray beam can have an energy of 40 to 60 keV. The x-ray source can be located within a source window through a sidewall of the production pipe on the first side of the production pipe. A processor system can be in communication with the attenuation detector, the scattered fluorescence detector, and the peak fluorescence detector to determine a density of the fluid, a density of an oil of the fluid, and a concentration of an ion within a brine of the fluid.

BRIEF DESCRIPTION OF THE DRAWINGS

So that the manner in which the above-recited features, aspects and advantages of the disclosure, as well as others that will become apparent, are attained and can be understood in detail, a more particular description of the disclosure briefly summarized above may be had by reference to the embodiments thereof that are illustrated in the drawings that form a part of this specification. It is to be noted, however, that the appended drawings illustrate only preferred embodiments of the disclosure and are, therefore, not to be considered limiting of the disclosure's scope, for the disclosure may admit to other equally effective embodiments.

Figure 1:
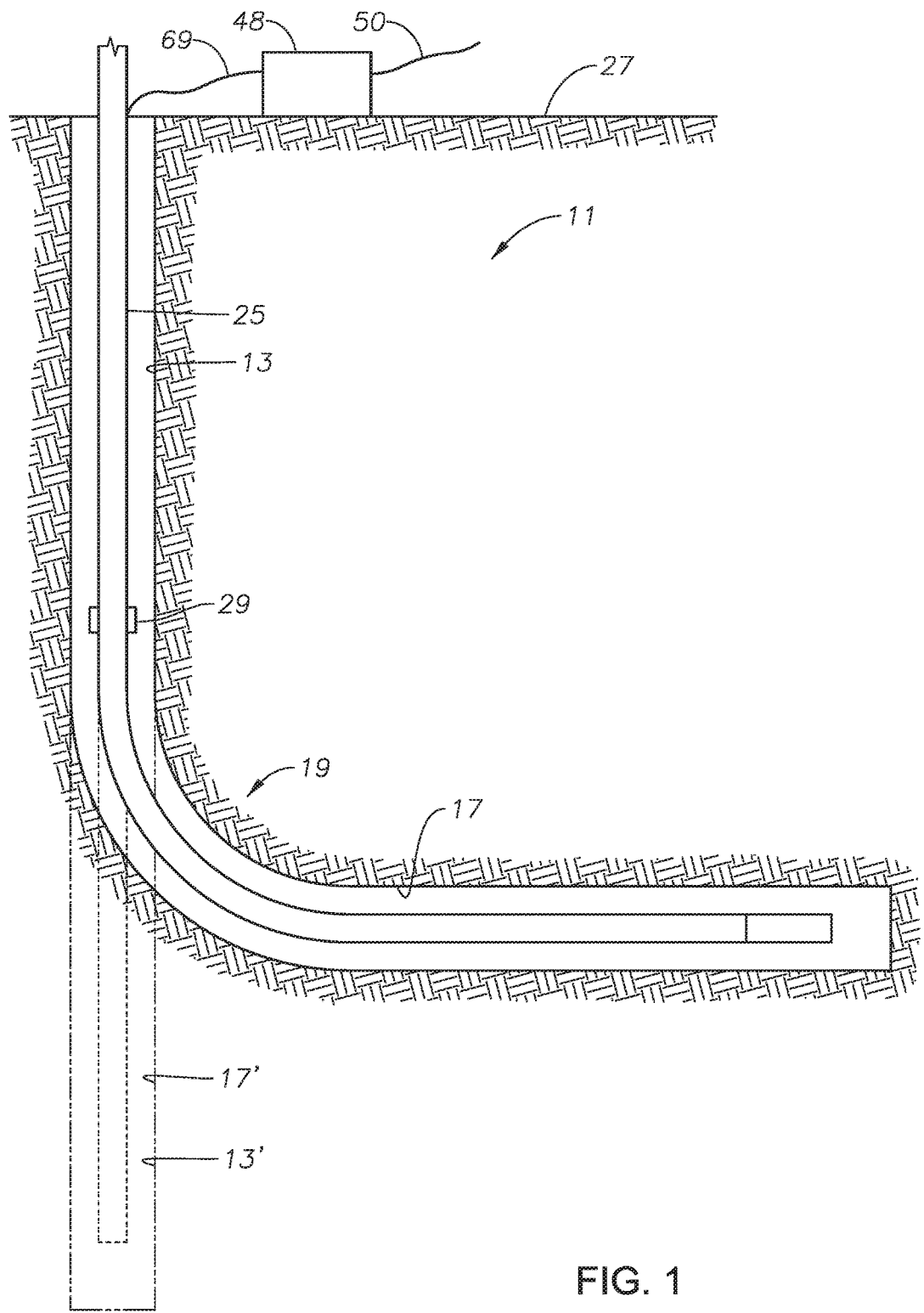
FIG. 1 is a schematic section elevation view of a subterranean well with a detection system in accordance with an embodiment of this disclosure.

DETAILED DESCRIPTION OF THE
EXEMPLARY EMBODIMENTS

Embodiments of the present disclosure will now be described more fully hereinafter with reference to the accompanying drawings which illustrate embodiments of the disclosure. This disclosure may, however, be embodied in many different forms and should not be construed as limited to the illustrated embodiments set forth herein. Those of skill in the art understand that the disclosure is not limited to or by the description of embodiments given in the Specification. Rather, these embodiments are provided so that this disclosure will be thorough and complete, and will fully convey the scope of the disclosure to those skilled in the art. Like numbers refer to like elements throughout, and the prime notation, if used, indicates similar elements in alternate embodiments or positions.

In the following discussion, numerous specific details are set forth to provide a thorough understanding of the present disclosure. However, it will be obvious to those skilled in the art that the systems and methods of the present disclosure can be practiced without such specific details. Additionally, for the most part, details concerning well drilling, reservoir testing, well completion and the like have been omitted inasmuch as such details are not considered necessary to obtain a complete understanding of the present disclosure, and are considered to be within the skills of persons skilled in the relevant art.

Those of skill in the art also understand that the terminology used for describing particular embodiments does not limit the scope or breadth of the disclosure. In interpreting this disclosure, including the appended Claims, all terms should be interpreted in the broadest possible manner consistent with the context of each term. All technical and scientific terms used in this disclosure, including the appended Claims have the same meaning as commonly understood by one of ordinary skill in the art to which this disclosure belongs unless defined otherwise.

As used herein, the singular forms "a", "an" and "the" include plural references unless the context clearly indicates otherwise. The referenced elements, components or steps may be present, utilized or combined with other elements, components or steps not expressly referenced. "Associated" and its various forms means something connected with something else because they occur together or that one produces the other. "Detect" and its conjugated forms should be interpreted to mean the identification of the presence or existence of a characteristic or property. "Determine" and its conjugated forms should be interpreted to mean the ascertainment or establishment through analysis or calculation of a characteristic or property Spatial terms describe the relative position of an object or a group of objects relative to another object or group of objects. The spatial relationships apply along vertical and horizontal axes. Orientation and relational words, including "uphole" and "downhole", are for descriptive convenience and are not limiting unless otherwise indicated.

Where this disclosure, including the appended Claims, provide a range of values, it is understood that the interval encompasses each intervening value between the upper limit and the lower limit as well as the upper limit and the lower limit. The disclosure encompasses and bounds smaller ranges of the interval subject to any specific exclusion provided.

Where this disclosure, including the appended Claims, reference a method comprising two or more defined steps, the defined steps can be carried out in any order or simultaneously except where the context excludes that possibility.

Looking at FIG. 1, subterranean well system 11 includes borehole 13. In the illustrated embodiment, borehole 13 includes lateral bore 17 having heel 19 and toe 21 extending horizontally from borehole 13. Production pipe 25 extends into borehole 13 of subterranean well system 11 and conveys fluids that are within the well to an earth's surface 27. In an alternate illustrated embodiment of FIG. 1, borehole 13' has a vertical bore 17'. Detection system 29 is associated with production pipe 25, as will be further described herein. In other alternate embodiments, detection system 29 can be associated with other pipelines or tubular members where there is a requirement to measure the properties of an entrained multiphase fluid flow.

Figure 2:
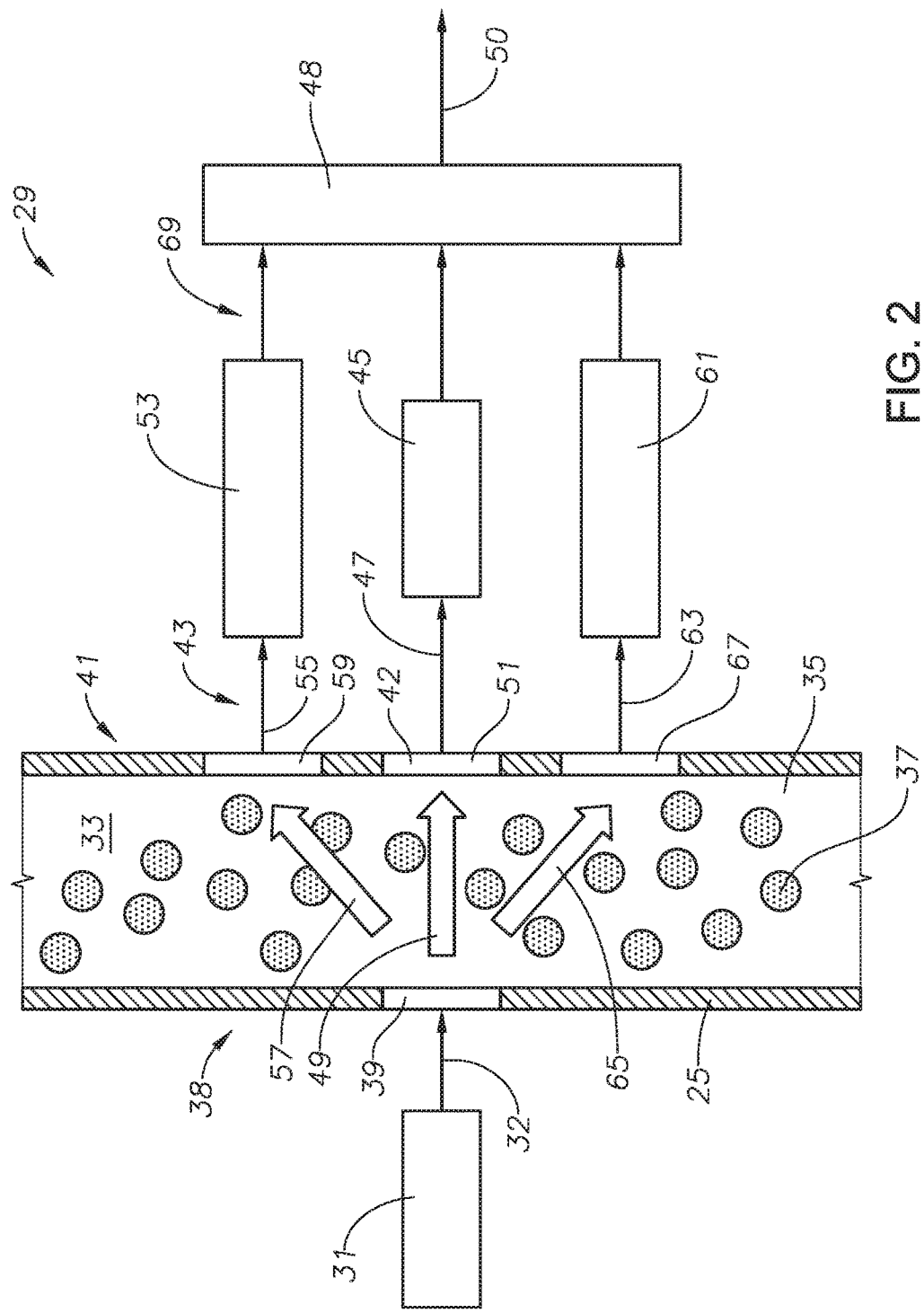
FIG. 2 is a schematic view of the detection system of FIG. 1.

Turning to FIG. 2, detection system 29 includes x-ray source 31. X-ray source 31 is a single and sole x-ray source utilized and required. X-ray source 31 is used to illuminate the fluids within production pipe 25, such as multiphase mixture 33. In the example of FIG. 2, multiphase mixture 33 consists of a continuous medium of crude oil 35 with droplets of water or brine 37 contained within the crude oil 35. Note that in alternate producing wells, the water can vary from 0-100% of the multiphase mixture, so phase inversion could occur where the continuous phase is brine 37 and the dispersed droplets can be oil 35. Although embodiments described in this disclosure are described in terms of the oil 35 being the continuous phase and the brine 37 being the dispersed droplets, systems and method described in this disclosure apply equally to embodiments with the continuous phase is brine 37 and the dispersed droplets is oil 35. In addition, systems and methods of this disclosure are also applicable to multiphase mixtures 33 that additionally contain a gas.

X-ray source 31 can have an energy of 40-70 keV. In a preferred embodiment, x-ray source 31 can have an energy of 50 keV, which equates to a wavelength of 0.035 nm. The x-ray beams 32 provided by x-ray source 31 penetrate multiphase mixture 33 and are attenuated by the presence of oil 35 and brine 37. By quantifying this attenuation, and knowing the attenuation coefficients of brine 37 and oil 35, it is possible to determine the mean density of multiphase mixture 33 and hence the water cut, as will be further described herein.

X-ray source 31 is located outside of a first side 38 of production pipe 25. X-ray source 31 can have, for example, a traditional vacuum tube type of construction. Alternately, x-ray source 31 can include cold cathode emission from nanotubes such that described by K. Kawakita, K. Hata, H. Sato, Y. Saito, "*Development of Microfocused X-Ray Source Using Carbon Nanotube Field Emitter*", J. Vac. Sci. Technol. B 24, 950 (2006), or through the development of microminiature X-ray tubes, such as, for example, those described in U.S. Pat. No. 8,300,769B2. For deployment within borehole 13, x-ray source 31 could be encapsulated within source window 39.

In order for x-ray source 31 to illuminate the multiphase mixture 33, x-ray source 31 directs x-ray beams 32 into production pipe 25. X-ray beams 32 can pass into production pipe 25 through source window 39. Source window 39 is located through a sidewall of production pipe 25 on the first side 38 of production pipe 25. Source window 39 can be transmissive enough to allow the x-ray beams 32 to pass through source window 39 and into production pipe 25. In alternate embodiments, x-ray source is of sufficient power that x-ray beams 32 can pass straight through the steel wall of production pipe 25, or through the use of a lighter but structurally strong material with a low x ray attenuation coefficient, such as PEEK. X-ray beams 32 pass into and through multiphase mixture 33 and out an opposite side 41 of production pipe 25 through an outgoing window 42 as resulting beam 43.

Detection system 29 also includes attenuation detector 45. Attenuation detector 45 can be located outside of the opposite side 41 of production pipe 25 and can detect or measure a level of attenuation of an attenuation beam 47 of resulting beam 43. The information obtained by attenuation detector 45 can be transmitted to processor system 48, which is in communication with attenuation detector 45. Attenuation beam 47 is a segment or portion of resulting beam 43. X-ray beams 32 are attenuated by multiphase mixture 33.

Oil 35 in multiphase mixture 33 has a particular attenuation coefficient, and brine 37 in multiphase mixture 33 has a different attenuation coefficient. The level of attenuation across the flow of multiphase mixture 33 flowing through production pipe 25 provides an estimate of the mean density of multiphase mixture 33. Because the attenuation coefficient is a function of density, information derived by attenuation detector 45 can be used to measure a density of multiphase mixture 33. By first knowing the oil 35 density from a phase behavior pressure, volume and temperature, or PVT analysis at the earth's surface 27, and extrapolating such information to downhole conditions, as well as knowing the brine 37 composition and hence brine 37 density (which is incompressible to first order), the mean density of multiphase mixture 33 can be used to estimate the water cut in a 0-100% range for oil water multiphase mixture 33 in an in-situ determination, as will be further described herein.

Utilizing actual data regarding characteristic of oil 35 and brine 37 that are calculated in-situ, as will be further described in this disclosure, will improve the accuracy of the water cut calculation compared to a theoretical estimation. In addition, the calculation being performed in-situ negates the need for a later or continuing PVT analysis for determining such characteristics. The calculation procedures can be performed by processor system 48. Processor system 48 can be an embedded PC running an operating system, or can be an alternate form of firmware. Processor system 48 can be located within borehole 13, or can be located at earth's surface 27. An output 50 from processor system 48 can be delivered to an operator at earth's surface 27. Output 50 can include the results of the detections, measurements, and calculations described in this disclosure.

In order to detect the level of attenuation, a first portion 49 of x-ray beam 32 passes through multiphase mixture 33 and passes out of production pipe 25 by way of detection window 51 as attenuation beam 47. Detection window 51 is one of a number of outgoing windows 42 and can be similar in construction to source window 39. Attenuation detector 45 should be sensitive to attenuation beam and be a standard vacuum tube apparatus that can be deployed in a permanent completion at elevated temperatures. In alternate embodiments, attenuation detector 45 can be an SiC detector using, as an example, the technology described by J. E. Lees, A. M. Barnett, D. J. Bassford, R. C. Stevens, A. B. Horsfall, "*SiC*

*X-ray Detectors for Harsh Environments*", J. Inst. 6 (2011) C01032, and can be deployed and encapsulated in detection window 51 in a similar way to x-ray source 31.

Detection system 29 can also include scattered fluorescence detector 53, which is a fluorescence x-ray spectrometer. Scattered fluorescence detector 53 can be located outside of the opposite side 41 of production pipe 25 and can detect or measure a fluorescence spectra of scattered fluorescence 55 of resulting beam 43. Scattered fluorescence 55 is a segment or portion of resulting beam 43. X-ray beams 32 cause oil 35 contained within multiphase mixture 33 to fluoresce in a particular frequency band of energies which can be used for chemometric analysis to determine the relative density or API of oil 35. For oil 35 the frequency range or energy level of the scattered fluorescence can be in the range of 18 to 23 keV, however the range of frequencies should be independent from any emissions expected from brine 37 and because brine 37 itself may include a wide range of different ions with different spectral properties, the range of frequencies can be adaptively configured for various applications.

In order to detect the fluorescence spectra, a second portion 57 of x-ray beam 32 passes through multiphase mixture 33 and passes out of production pipe 25 by way of scattered fluorescence window 59 as scattered fluorescence 55. Scattered fluorescence window 59 is one of the outgoing windows 42, which can be transparent to x-rays in the range between 18-23 keV. Scattered fluorescence window 59 can be tailored from similar materials as source window 39. As an example, scattered fluorescence window 59 can be formed of PEEK and alternately, can be optimized through practical experimentation.

In order to calibrate the chemometric response to different oils 35, laboratory characterization of representative oil of sufficiently varying API's can be performed in representative downhole conditions within a pressure cell. This will generate a series of fluorescence spectra which will evolve as the API of the oil is incremented. Although the technique is being described as an example, for API classification, similar approaches can be taken with different measurands. Principal component analysis is a technique that can be used to condense the obtained spectra into a reduced dimension set where the principal component scores can be calculated as PC1, PC2, PC3, PC4 . . . PCn. A description of how principal component analysis can be applied to fluorescence spectroscopy is provided in L. Nørgaard, R. Bro, S. B. Engelsen, *"Principal Component Analysis and Near Infrared Spectroscopy"*, Foss Corporation, White Paper, except that in the example embodiment of this disclosure, only the API of the oil is varied.

A representative samples of crude oil from fields would be obtained, and PVT analysis would be performed to understand the composition of the crude oil. As a first attempt, spectra would be obtained for each of the crude oils, and the resulting spectrum would be associated with the particular API. Using an example energy level of 18 keV to 23 keV, the fluorescence spectra can be sampled in the approximate range from 18 keV to 23 keV in quantized steps of sufficient resolution to resolve individual structure within the measurement. At each individual energy measurement point, an average spectral value from all the different API measurements shall be performed to construct an averaged fluorescence spectrum. Subsequently, the difference between individual API spectra and the mean spectrum shall be computed to generate a mean centered set of spectra. Using this as an input, principal component analysis can be applied to generate the principal component values PC1, PC2, PC3, . . . PCn. An example of such procedure is described in E-C. Shin, B. D. Craft, R. B. Pegg, R. D. Phillips, R. R. Eitenmiller, *"Chemometric Approach to Fatty Acid Profiles in Runner Type Peanut Cultivars by Principal Component Analysis (PCA)"*, Food Chemistry 119 (2010) 1262-1270. Each API measurement will generate a different set of PC1, PC2, PC3, . . . PCn values.

Taking the first three values as an illustrative example for a given API measurement, PC1, PC2, PC3 can define a point in 3 dimensional space (PC1, PC2, PC3). As the API is varied, this point will move through the space. By fitting a best fit line through the 3 dimensional cluster of points, an ideal calibration curve can be defined which maps on to the API values. The equation of this line shall be a function of API, and this can be used to calibrate subsequent real world measurements of crude oil spectra. In this case for an individual spectrum, the point in space (PC1, PC2, PC3) can be computed, and this will either correspond with or have a corresponding closest point on the calibration line described previously. In the example embodiment described herein, this point can be associated with a particular value of API. Although API is described in this embodiment as the single parameter being evaluation, the procedure could be extended to take multiple other variables that can be obtained into consideration. For example, PVT analysis can account for potential degeneracy in computed PC1, PC2, PC3, . . . PCn values. The calibration of the principal component analysis can be performed separately in a laboratory setting outside of detection system 29 and once the calibration has been established, the calibration can be implemented as an algorithm embedded or coded on to processor system 48 of detection system 29 to allow for in-situ determination of the API. After such initial calibration, water cut can be calculated in-situ in real time with detection system 29.

Scattered fluorescence detector 53 can be in communication with processor system 48 and provide a measurement of the fluorescence spectrum in the form of a one dimensional vector of real numbers. By calculating the specific values of PC1, PC2, . . . PCn a measured point in the multidimensional space defined by an orthogonal set of principal component vectors can be determined. By calculating the intersection or the resultant point on the calibration curve that is closest to the measured point that was obtained as described above, it is possible to correlate the spectrum with an API value obtained from the calibration curve. The resultant point can be located by, for example, implementing a minimization algorithm. This processing can be performed within processor system 48. Because oil 35 has a relatively low molecular weight, x-ray beams 32 will not be strongly attenuated, however x-ray beam 32 can be sufficiently attenuated to allow chemometric techniques of this disclosure be able to classify different API's or other properties of oil 35. Knowing the density of oil 35 as determined within borehole 13 can also improve the accuracy of the water cut of multiphase mixture 33. Processor system 48 can therefore utilize the density of oil 35, as determined from the scattered fluorescence 55, to improve the accuracy of the water cut calculation.

Detection system 29 can also include peak fluorescence detector 61 that is a second fluorescence x-ray spectrometer. Peak fluorescence detector 61 can be located outside of the opposite side 41 of production pipe 25 and can detect or measure a fluorescence peak of specific fluorescence 63 of resulting beam 43. Specific fluorescence 63 is a segment or portion of resulting beam 43. In order to detect the fluorescence spectra, a third portion 65 of x-ray beam 32 passes through multiphase mixture 33 and passes out of production pipe 25 by way of specific fluorescence window 67 as specific fluorescence 63. Specific fluorescence window 67 is one of the outgoing windows 42, and can be transmissive to the wavelength of specific fluorescence 63.

Specific fluorescence 63 can be a result of the presence of ions within brine 37 of multiphase mixture 33. As multiphase mixture 33 is illuminated by x-ray beams 32, specific ions fluoresce at known wavelengths. Peak fluorescence detector 61 is tuned to monitor only the wavelength of fluorescence of the ion of interest. In an example embodiment as an illustrative example, sodium ions fluoresce at a wavelength of 1.191 nm. Specific fluorescence window 67 is transmissive to the wavelength of the ions of interest so that in the example where sodium ions are being detected and measured, specific fluorescence window 67 is transmissive to specific fluorescence 63 with a wavelength of 1.191 nm. In alternate embodiments, a number of different ions can be detected in parallel by implementing a parallel set of peak fluorescence detectors 61 and filters tuned to pass the wavelength associated with the ion in question so that ions present in brine 37 which also fluoresce can be considered.

In order to detect and measure the fluorescence peak of specific fluorescence 63, the intensity of x-ray source 31 should be to be sufficiently large to penetrate the full diameter of multiphase mixture 33 across production pipe 25. X-ray source 31 with an energy of 50 keV should yield specific fluorescence 63 that is detectable by peak fluorescence detector 61, however the wavelength of x-ray beams 32 may be tuned to ensure efficient coupling between the wavelength of x-ray beams 32 and the resulting fluorescence. The use of a diffraction grating with an appropriately mounted sensor, sensitive to the 1.191 nm radiation can also be used to improve results.

The intensity of the chosen florescence peak increases and decreases as a function of the number of ions present and the information obtained by peak fluorescence detector 61 can therefore be used as a measure of the concentration of the ion within brine 37 within multiphase mixture 33. In the example embodiment of detecting sodium ions, the salinity of brine 37 can be determined. Processor system 48 is in communication with peak fluorescence detector 61 and can use the value of the measured intensity of the florescence peak obtained by peak fluorescence detector 61 to calculate the concentration of the ion within brine 37. A ratiometric measurement and procedure can be used by processor system 48 where the specific fluorescence 63 is scaled relative to an attenuation beam 47 to give an estimate of ion concentration within brine 37, independent of attenuation caused by different distributions of multiphase mixture 33. Such an approach can be calibrated experimentally. Knowing the concentration of an ion of brine 37 as determined within borehole 13 can also improve the accuracy of the water cut of multiphase mixture 33. Processor system 48 can therefore utilize the concentration of an ion of brine 37, as determined from the specific fluorescence 63, to improve the accuracy of the water cut calculation.

Looking at FIGS. 1-2, in an example of operation, to determine characteristics of the fluid, such as multiphase mixture 33, in a subterranean well, production pipe 25 can be lowered into borehole 13 and fluids can be produced through production pipe 25 to the earth's surface 27. X-ray source 31 can direct x-ray beam 32 into multiphase mixture 33 from first side 38 of production pipe 25. X-ray beam 32 will exit directing production pipe 25 through an opposite side 41 of production pipe 25 as resulting beam 43. Resulting beam 43 can have various components, including attenuation beam 47, scattered fluorescence 55, and a specific fluorescence 63. Attenuation detector 45 can detect a level of attenuation in attenuation beam 47, scattered fluorescence detector 53 can detect a fluorescence spectra of scattered fluorescence 55, and peak fluorescence detector 61 can detect a fluorescence peak of specific fluorescence 63.

Processor system 48, which is in communication with attenuation detector 45, scattered fluorescence detector 53, and peak fluorescence detector 61 through communications lines can receive information from each of attenuation detector 45, scattered fluorescence detector 53, and peak fluorescence detector 61. Processor system 48 can perform the calculations required to determine a water cut of multiphase mixture 33 with improved accuracy by using information received from attenuation detector 45, scattered fluorescence detector 53, and peak fluorescence detector 61. Information derived by attenuation detector 45 can be used to measure a density of multiphase mixture 33. The density of oil 35 of multiphase mixture 33 can be calculated by processor system 48 with information received from scattered fluorescence detector 53. The concentration of an ion within brine 37 of multiphase mixture 33 can be calculated by processor system 48 with information received from peak fluorescence detector 61. In this way, the systems and methods described herein are able to provide information about the average density of multiphase mixture 33 and density or API of oil 35, as well as information regarding brine composition, thereby providing a water cut measurement without the need for ongoing calibration using fluid density inputs, since the density of multiphase mixture 33 and the density of oil 35 of multiphase mixture 33 are both determined by direct measurement.

Embodiments of the present disclosure described herein, therefore, are well adapted to carry out the objects and attain the ends and advantages mentioned, as well as others inherent therein. While a presently preferred embodiment of the disclosure has been given for purposes of disclosure, numerous changes exist in the details of procedures for accomplishing the desired results. These and other similar modifications will readily suggest themselves to those skilled in the art, and are intended to be encompassed within the spirit of the disclosure and the scope of the appended claims.

What is claimed is:

1. A method for determining characteristics of a fluid in a subterranean well, the method comprising:
   providing a production pipe extending into the subterranean well, the production pipe sized to produce the fluid from within the subterranean well to an earth's surface;
   locating an x-ray source on a first side of the production pipe within the subterranean well;
   directing an x-ray beam into the production pipe and into the fluid, and out of an opposite side of the production pipe as a resulting beam, with the x-ray source;
   detecting a level of attenuation of the resulting beam with an attenuation detector located on an opposite side of the production pipe within the subterranean well;
   detecting a fluorescence spectra of the resulting beam with a scattered fluorescence detector located on the opposite side of the production pipe within the subterranean well; and
   detecting a fluorescence peak of the resulting beam with a peak fluorescence detector located on the opposite side of the production pipe within the subterranean well.

2. The method according to claim 1, wherein:
the production pipe has a source window through a sidewall on the first side of the production pipe and an outgoing window through the sidewall on the opposite side of the production pipe;
the step of directing the x-ray beam into the production pipe includes passing the x-ray beam into the production pipe through the source window; and
the step of directing the x-ray beam out of an opposite side of the production pipe as the resulting beam includes passing the x-ray beam out of the production pipe through the outgoing window.

3. The method according to claim 2, wherein the step of directing the x-ray beam out of an opposite side of the production pipe as the resulting beam further includes:
directing an attenuation beam of the resulting beam through a detection window of the outgoing window;
directing a scattered fluorescence of the resulting beam through a scattered fluorescence window of the outgoing window; and
directing a specific fluorescence of the resulting beam through a specific fluorescence window of the outgoing window.

4. The method according to claim 3, wherein the step of detecting the scattered fluorescence of the resulting beam includes detecting the scattered fluorescence having an energy of 18 to 23 keV.

5. The method according to claim 1, wherein the step of detecting the fluorescence peak includes detecting the fluorescence peak with a wavelength of 1.191 nm.

6. The method according to claim 1, further comprising a processor system in communication with the attenuation detector, the scattered fluorescence detector, and the peak fluorescence detector, the method further comprising determining a density of the fluid, a density of an oil of the fluid, and a concentration of an ion within a brine of the fluid with the processor system.

7. The method according to claim 6, further comprising calculating a water cut value with the density of the fluid, the density of the oil and the concentration of the ion with the processor system.

8. A method for determining characteristics of a fluid in a subterranean well, the method comprising:
locating an x-ray source on a first side of a production pipe within the subterranean well, the production pipe extending into the subterranean well and sized to produce the fluid from within the subterranean well to an earth's surface;
directing an x-ray beam with the x-ray source into the production pipe and into the fluid, and out of an opposite side of the production pipe as an attenuation beam, a scattered fluorescence, and a specific fluorescence;
detecting a level of attenuation of the attenuation beam with an attenuation detector located within the subterranean well and determining a density of the fluid from the level of attenuation;
detecting a fluorescence spectra of the scattered fluorescence with a scattered fluorescence detector located within the subterranean well and determining a density of an oil of the fluid with the fluorescence spectra; and
detecting a fluorescence peak of the specific fluorescence with a peak fluorescence detector located within the subterranean well and determining a concentration of an ion within a brine of the fluid with the fluorescence peak.

9. The method according to claim 8, further comprising determining a water cut of the fluid using the level of attenuation, the fluorescence spectra and the fluorescence peak.

10. The method according to claim 8, further comprising a processor system, the processor system performing the steps of determining the density of the fluid, determining the density of the oil, and determining the concentration of the ion.

11. The method according to claim 8, further comprising:
directing the attenuation beam through a detection window of the production pipe;
directing the scattered fluorescence through a scattered fluorescence window of the production pipe; and
directing the specific fluorescence through a specific fluorescence window of the production pipe.

12. A system for determining characteristics of a fluid in a subterranean well, the system comprising:
a production pipe extending into the subterranean well and sized to produce the fluid from within the subterranean well to an earth's surface;
an x-ray source located on a first side of the production pipe within the subterranean well and directing an x-ray beam into the production pipe and into the fluid, and out of an opposite side of the production pipe as a resulting beam;
an attenuation detector located on an opposite side of the production pipe within the subterranean well, selectively detecting a level of attenuation of the resulting beam;
a scattered fluorescence detector located on the opposite side of the production pipe within the subterranean well, selectively detecting a fluorescence spectra of the resulting beam; and
a peak fluorescence detector located on the opposite side of the production pipe within the subterranean well, selectively detecting a specific fluorescence of the resulting beam.

13. The system according to claim 12, wherein the production pipe has a source window through a sidewall on the first side of the production pipe and an outgoing window through the sidewall on the opposite side of the production pipe, the x-ray beam passing into the production pipe through the source window and the resulting beam passing out of the production pipe through the outgoing window.

14. The system according to claim 13, wherein the outgoing window has a detection window through which an attenuation beam of the resulting beam passes, a scattered fluorescence window through which a scattered fluorescence of the resulting beam passes, and a specific fluorescence window through which a fluorescence peak of the resulting beam passes.

15. The system according to claim 14, wherein the scattered fluorescence window is transparent to the scattered fluorescence having an energy of 18 to 23 keV.

16. The system according to claim 14, wherein the specific fluorescence window is transmissive to a wavelength of the specific fluorescence.

17. The system according to claim 12, wherein the specific fluorescence has a wavelength of 1.191 nm.

18. The system according to claim 12, wherein the x-ray source is located within a source window through a sidewall of the production pipe on the first side of the production pipe.

19. The system according to claim 12, further comprising a processor system in communication with the attenuation detector, the scattered fluorescence detector, and the peak fluorescence detector to determine a density of the fluid, a density of an oil of the fluid, and a concentration of an ion within a brine of the fluid.

20. The system according to claim 12, wherein the x-ray beam has an energy of 40 to 60 keV.

21. A method for determining characteristics of a fluid in a subterranean well, the method comprising:
  providing a production pipe extending into the subterranean well to convey the fluid from within the subterranean well to an earth's surface;
  locating an x-ray source on a first side of the production pipe;
  directing an x-ray beam into the production pipe and into the fluid, and out of an opposite side of the production pipe as a resulting beam, with the x-ray source;
  detecting a level of attenuation of the resulting beam with an attenuation detector located on an opposite side of the production pipe;
  detecting a fluorescence spectra of the resulting beam with a scattered fluorescence detector located on the opposite side of the production pipe;
  detecting a fluorescence peak of the resulting beam with a peak fluorescence detector located on the opposite side of the production pipe;
  determining a density of the fluid, a density of an oil of the fluid, and a concentration of an ion within a brine of the fluid with the processor system with a processor system in communication with the attenuation detector, the scattered fluorescence detector, and the peak fluorescence detector; and
  calculating a water cut value with the density of the fluid, the density of the oil and the concentration of the ion with the processor system.

* * * * *